United States Patent [19]

Hafeman et al.

[11] Patent Number: 5,164,319
[45] Date of Patent: Nov. 17, 1992

[54] MULTIPLE CHEMICALLY MODULATED CAPACITANCE DETERMINATION

[75] Inventors: Dean G. Hafeman, San Bruno; Harden M. McConnell, Stanford, both of Calif.

[73] Assignee: Molecular Devices Corporation, Palo Alto, Calif.

[21] Appl. No.: 438,675

[22] Filed: Nov. 17, 1989

Related U.S. Application Data

[63] Continuation of Ser. No. 768,977, Aug. 22, 1985, abandoned.

[51] Int. Cl.[5] .............................................. C12M 1/34
[52] U.S. Cl. .................................... 435/291; 204/403; 204/400; 435/287
[58] Field of Search ............... 435/291, 287; 204/403, 204/195 R

[56] References Cited

U.S. PATENT DOCUMENTS

| | | | |
|---|---|---|---|
| 4,020,830 | 5/1977 | Johnson et al. | 128/2 |
| 4,062,750 | 12/1977 | Butler | 204/403 X |
| 4,072,576 | 2/1978 | Arwin et al. | 435/291 |
| 4,218,246 | 8/1980 | Koshiishi | 364/571 |
| 4,225,410 | 9/1980 | Pace | 204/195 R |
| 4,397,714 | 8/1983 | Janata et al. | 204/1 T |
| 4,490,216 | 12/1984 | McConnelll | 204/1 T |
| 4,571,543 | 2/1986 | Raymond et al. | 324/425 |

OTHER PUBLICATIONS

"Investigation of the Ion Selectivity Mechanism of Hydrogen Ion–Sensitive Field Effect Transistors (ISFET)", Vlasou et al, 3rd Symposium on Ion-Selective Electrodes, pp. 387-397.

Primary Examiner—Larry Jones
Attorney, Agent, or Firm—Allegretti & Witcoff, Ltd.

[57] ABSTRACT

Apparatus and methods are provided for multiple detection of analytes employing semiconductor capacitance as the signal modulated by the analyte. A plurality of semiconductor capacitors are organized for detection (at individual sites) of changes in capacitance which are related to changes in a fluid medium, where the change can be related to the presence of an analyte. Circuitry is designed to substantially maximize sensitivity.

10 Claims, 4 Drawing Sheets

MULTIPLE CHEMICALLY MODULATED CAPACITANCE DETERMINATION

This is a continuation of application Ser. No. 768,977, filed Aug. 22, 1985, now abandoned.

BACKGROUND OF THE INVENTION

1. Field of the Invention

The detection of the presence of a material and/or its amount in a particular environment becomes increasingly important in a society which seeks to monitor and manipulate its environment. Despite the long history of developing devices for measurement of various materials in liquid media, there still remain ample opportunities for improvements in sensitivity, efficiency, economy, and ease of use. Among the manifold detection methods, one device which has found recent application is the field effect transistor (FET) and various modifications of the device. Various studies have been directed to the use of FETs for measurement of organic molecules. See for example, Stenberg et al., *J. Coll. Interface and Sci.* (1979) 72:255-264; Bergveld and De-Rooij, *Med Biol. Eng. Compt.* (1979) 17:647-654; Bergveld et al., *IEEE Trans. BMI*-23 (1976) pages 136-144; and Lauks and Zemel; *IEEE Trans. on Electron Devices,* Vol. ED-26, No. 12 (December 1979), pages 10959-10964. These references are merely illustrative of references directed to semiconductor device, particularly field effect transistors, for measurement of material in solution. The FET devices have not found commercial acceptance and in many sitations, lack flexibility. For use as chemical detectors, FET devices particularly suffer from the difficulty of obtaining exposed gate regions and working with them in an experimental environment.

As compared to other devices, semiconductive or other devices which respond to an electrical signal provide for a number of advantages. The electrically responsive device can respond to relatively small signals. Furthermore, by various techniques, the signal can be modulated and the background noise diminished or substantially eliminated. Electrical devices can frequently be miniaturized, so that relatively small equipment can be developed for measurement of changes in various fluids.

2. Description of the Prior Art

References of interest include Gronet and Lewis, *Nature* (1982) 300:733-735; Bard and Faulkner, 1980. *Electrochemical Methods—Fundamentals and Applications,* John Wiley and Sons, New York; Fahrenbruch and Bube, 1983. *Fundamentals of Solar Cells—Photovoltaic Energy Conversion,* Academic Press, New York; Fonash, 1981; *Solar Cell Device Physics,* Academic Press, New York; and *Photoeffects at Semiconductor-Electrolyte Surfaces,* ed. Nozik, American Chemical Society, Washington, D.C., 1981. See also U.S. Pat. No. 4,293,310 and PCT Application No. WO83/02669. Of particular interest to the measurement of solution pH with a semiconductor electrode is Y. G. Vlasov, A. J. Bratov, and V. P. Letavin, *In: Ion-Selective Electrodes* 3, *Analytical Chemistry Symposium Series Vol.* 8 (E. Pungor, Ed.) Elsevier Publ. Co., Amsterdam, 1981; Luc Bousse, *Thesis,* Twente University, The Netherlands, 1982; M. T. Pham and W. Hoffman, *Sensors and Actuators* (1984) 5:217-228; F. Chauvet and A. Amari, *Sensors and Actuators* (1984) 6:255-267; whose disclosures are incorporated herein by reference.

SUMMARY OF THE INVENTION

Apparatus and methods are provided for determining a characteristic of a medium which affects the capacitance of a semiconductor electrode. A liquid sample medium is placed between the semiconductor electrode and a counter electrode. The semiconductor electrode is coated with an insulating layer. The insulating layer acts as a dielectric to form a first capacitor. A second capacitor, in series with the first, is formed by the "space charge layer" in the semiconductor immediately under (subjacent to) the insulating layer. The capacitance of this second capacitor varies with the application of (externally supplied) DC bias voltage. Because the liquid sample medium provides a surface potential on the exposed surface of the insulating layer, and because this potential is in series with the applied D bias voltage, the capacitance of the second capacitor can vary due to the state of the liquid sample medium. A plurality of series capacitor pairs for measuring a plurality of analytes are formed by using a number of isolated semiconductor electrodes and a single counter electrode or a number of counter electrodes and a single semiconductor electrode.

A monolithic semiconductor wafer is used for the semiconductor electrode in one embodiment, with a number of isolated electrodes being formed by doping certain locations (electrode regions hereinafter referred to as "pixels") which are separated from other electrode regions by insulating regions. The individual pixels (electrode regions) are sequentially coupled to a circuit which applied both a DC bias voltage as well as a small alternating (modulating) voltage across the individual capacitors. The capacitive impedance determines the alternating current in response to the applied alternating voltage. This alternating current is measured and is proportional to the total capacitance of the first and second capacitors in series which is, in turn, related to the state of the sample medium. The DC bias voltage is applied to maintain the response to the medium in the most sensitive range by varying the capacitance of the semiconductor space-charge region. In the preferred mode of operation series capacitance is held constant, subsequent to a change in the state of the medium, by varying the DC bias voltage. The amount of change in DC bias voltage required to maintain a constant amplitude alternating current (and thus constant capacitance) is a sensitive measure of the surface potential on the insulator due to the nature of the liquid medium.

DESCRIPTION OF THE SPECIFIC EMBODIMENTS

Figure 1:
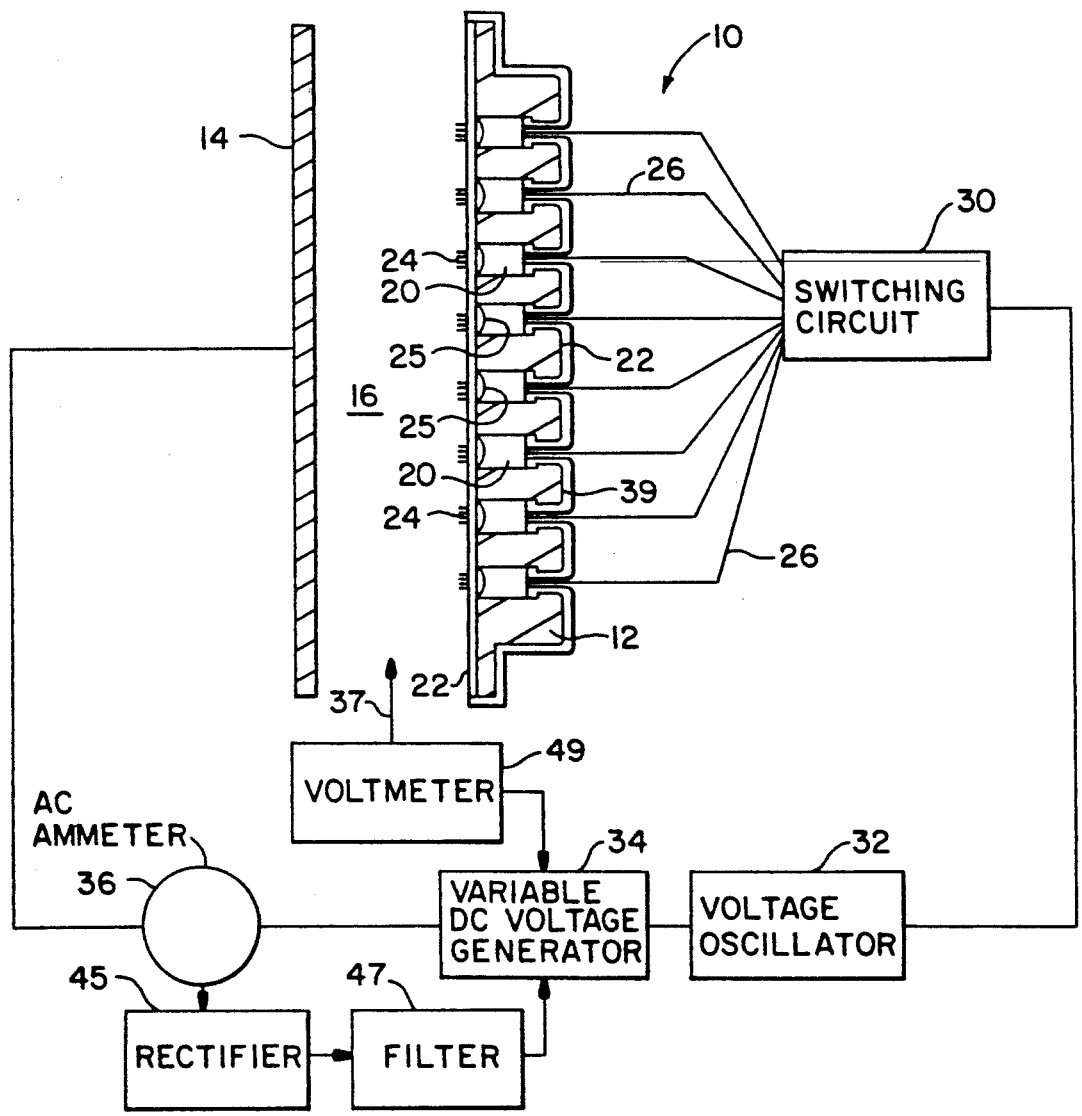
FIG. 1 is a schematic diagram of an embodiment of a device according to the subject invention.

In FIG. 1, the schematic drawing of a device according to this invention is shown in part in cross-section. The device 10 has a monolithic semiconductor electrode or plate 12. Facing the semiconductor electrode 12 is a facing plate or counter electrode 14. The two plates 12 and 14 define channel 16. The semiconductor electrode 12 may be p-doped or n-doped and has a plurality of regions 20 which are functionally isolated either by being oppositely doped or having an oppositely doped region from the bulk of the semiconductor electrode 12. The regions 20 are also referred to as "pixels" herein. Semiconductor electrode 12 is separated from channel 16 by an insulating layer 22.

In operation, an analyte fluid is introduced into channel 16 and separate, local chemical reactions occur at specific binding members 24, indicated as small hairs. The local chemical reactions will affect the local surface potential at the specific binding members 24 of the insulating layer 22. These local electric field which are created effectively alter the space charge capacitance of the semiconductor under the specific binding members 24. By measuring the combined series capacitance for each pixel 20, the degree of the chemical reaction can be determined. Reference should be made to the above-referenced article by Vlasov, Bratov and Letavin for a more complete description of the capacitive effect.

The semiconductor structure will be comprised of an insulative layer, which is substantially inert to the assay medium in channel 16, and either p- or n-type semiconducting material. In some situations it may be desirable to have the body of the semiconductor doped with one dopant and sites below the insulative layer oppositely dopes so as to have p-n junctions between individual pixels 20. When maintained under reverse bias conditions, these junctions are highly resistive and effectively isolate, electrically, individual pixels one from another.

In operation, the assay medium will be in contact with the insulative layer and will affect the surface potential at the interface of the liquid medium and the insulative layer. The capacitance of the insulative layer will be constant. The concentration of charge in the surface layer underneath the insulative layer, however, will vary with the potential of the liquid medium interface. This charge concentration will determine the capacitance of this layer. By measuring the capacitance of the two capacitors in series— the insulative layer and the adjacent layer in the semiconductor—one can measure changes in the surface potential at the interface of the medium and the insulative layer. By providing for reagents or protocols involving the assay medium, which result in a change in surface potential in relation to the presence and amount of a particular analyte, measurement of the capacitance or related electrical determination can be related to the presence and amount of analyte in the assay medium.

In order to provide for the substantially simultaneous determination of a plurality of samples, which samples may be the same or a different medium, two different embodiments may be employed. The first and preferred embodiment involves a plurality of pixels, each pixel having the construction described above and having an insulative layer and a semiconductor layer, where each pixel is insulated from each of the other pixels. Such electrical insulation may be effected either by an insulating (reverse-biased) p-n junction (junctional isolation) or by interposing nonconducting material between pixels (insulator isolation). The techniques employed in fabrication of such electrically insulated regions in a single monolithic semiconductor crystal are well known to those skilled in the art of semiconductor microfabrication. See, for example, I. Brodie and J. J. Muray, *The Physics of Microfabrication*, Plenum Press, New York, 1982; and S. M. Sze, *Physics of Semiconductor Devices*, 2nd Edition, Wiley-Interscience, New York, 1981. Alternatively, one may separately construct individual semiconductor electrodes, as described above, and place a multiplicity of these electrode on or in a matrix of material which effectively electrically isolates the electrodes one from another. In order for measurement of the semiconductor electrode potential, an external measuring circuit will be utilized. This circuit, or multiplicity of circuits, will make electrical contact, separately, with each of the pixels. In the case of a single circuit, separate electrical contact with each of the pixels is made in temporal sequence by means of an electrical switching mechanism. Additionally the external circuit(s) make contact with either a single counter electrode or a multiplicity of counter electrodes placed in the liquid sample medium. The second embodiment allows for the simultaneous determination of a plurality of a samples with a single uniform semiconductor electrode by means of a confronting conductive electrode, which is in contact with the assay medium and has a plurality of electrode plates, each plate effectively insulated from each of the other plates.

In the first preferred embodiment where the semiconductor electrode is comprised of a plurality of pixels, the pixel can be fabricated individually, but preferably will be part of a single semiconductor wafer. The semiconductor wafer may then be oppositely doped from the dopant of the wafer at a plurality of sites to define the pixels (junctional isolation). Various means may be provided for ensuring the insulation of each of the pixels from each other. A reverse bias potential (voltage) may be applied to the oppositely doped region in order to insure that the p-n junctions are maintaining in their nonconducting (reverse-biased) state. Ion or charge implantation in the region of the p-n junction may be used as another means of insuring that the junctions are maintained in the nonconducting state. Alternatively, the immediately surrounding area of each pixel may be eroded, so as to create a well between each pixel and the resulting islands and intervening areas modified to provide for an insulative layer. The insulative layer may be an oxide or nitride or a combination thereof. Of particular interest with silicon is the use of an oxynitride surface. Each of the pixels with have an independent contact to a circuit, so that any change in the electrical measurement by be individually determined. Various techniques can be employed for connecting the pixels individually to the external circuit.

In a second embodiment where the semiconductor electrode is of a uniform composition (that is, there is a semiconductor layer extending uniformly under the insulator layer or individual pixels are not insulated from each other) the confronting conducting electrode may be comprised of a plurality of individual plates. In order to provide for effective insulation between the individual plates, since each of the plates is immersed in the conducting aqueous medium, as previously indicated, it will be necessary that the plates be separated by very thin channel of sufficient length to provide for a substantial electrical isolation between the plates.

The semiconductor electrode will generally be composed of semiconductor material such as silicon, which may be a single crystal, polycrystalline or amorphous, gallium arsenide, gallium selenide, aluminum gallium arsenide, or the like. The semiconductor material will be either of the p- or n-type and, as appropriate, may employ such dopants as boron, aluminum, phosphorus, arsenic, antimony, or the like. The degree of doping may be varied widely, there being a wide variety of commercially-available doped wafers which can be used, where the body of the wafer is lightly doped and portions of the wafer heavily doped. The concentration of the dopant will normally vary empirically to provide the desired capacitance response, frequently being a matter of convenience, and will generally range from about $10^{12}$ to $10^{18}$ atoms/cc, usually for silicon, the resistivity will be about 0.01–100 ohm-cm.

In all cases, a change in the state of the medium causes a change in the semiconductor electrode capacitance. The electrode capacitance may be measured conveniently with the aid of an external capacitance measuring circuit. The external circuit may be one of several types commonly used to measure capacitance in electrochemical cells. See, for example, Bard and Faulkner, 1980. *Electrochemical Methods—Fundamentals and Application,* John Wiley and Sons, New York. The circuit may measure capacitance in a variety of ways including: a) determination of current as a result of a voltage step; b) determination of voltage as a result of a current step; c) determination of current as a function of a continuously changing voltage (voltage sweep); or d) determination of the quantity of electrical charge (current×time) necessary to charge the capacitors in series in the electrical circuit. The preferred method is c), particularly where a linear alternating voltage sweep (triangle wave) is applied and the amplitude of the steady-state current that results is measured. In this case, the series capacitance in the circuit is simply determined as the product of the steady-state current and the reciprocal of the voltage sweep rate. The circuits will be devised to provide maximal sensitivity for detecting small changes in the state of the medium. The observed signal from the circuit can be a result of a change in direct current, alternating current, or the effect of a direct current on an alternating current.

Where monolithic wafers are used, they may come in a variety of sizes and shapes, varying from chip size which may have its largest dimension of about 1.0 mm, usually at least 5 mm; or wafer size, which may be 500 mm, more usually not more than about 100 mm in its largest dimension. The electrode region will usually have at least one smooth surface or smooth portion of a surface, desirably flat, which will serve as the electrode surface. The wafer may be round, rectangular, elongate or the like. The thickness of the chip or wafer will generally be not more than about 2 mm, usually less than about 1 mm, and generally not less than about $0.05\mu$, usually not less than about 0.1 mm.

An insulative layer is employed to cover the electrode regions and may be uniformly coated over the entire structure. The significant factor is that the semiconducting portion of the semiconductor electrode is electrically insulated from the medium by some means. Conveniently, a coating of silicon oxide and/or silicon nitride can be employed generally of from about 200 to 2000 Å, preferably from about 600 to 1500 Å to provide for the insulative layer. The silicon oxide or nitride can be used by itself or in conjunction with other materials, or such other materials may be used substantially independently of the silicon oxide or nitride. That is various insulative coatings may be employed which are stable under the conditions of use and provide for the desired degree of insulation and capacitive response.

Depending upon the nature of the insulative coating and the manner of attachment to the surface, various techniques may be employed for providing the coating. Methods for providing coatings include spraying, painting, dipping, reacting with an active vapor, e.g., steam or ammonia, or a reactive reagent in solution, e.g., silyl chloride, vapor deposition, electro-deposition, or the like.

Silicon oxide layers can be achieved using oxygen or water vapor, controlling the thickness of the layer by the conditions employed, e.g., time and temperature. Silicon oxide coatings can also be obtained by electrodeposition. Silicon nitride layers can be obtained by reaction of silicon and nitrogen or reaction of compounds containing silicon and nitrogen such as dichlorosilane and ammonia. Standard methods of deposition of silicon nitride from the reaction of silanes and ammonia or nitrogen in the gas phase are well known to those skilled in the art of semiconductor microfabrication.

Alternatively, or in addition, compositions such as organosilanes can be bonded to the surface of the semiconductor electrode, so as to provide for an insulative layer and to allow for particular operations. The organo groups may be of from about 1 to 1000 carbon atoms, more usually of from about 1 to 25 carbon atoms, which may be aliphatic, alicyclic, aromatic or heterocyclic or combinations thereof, usually hydrocarbon, which may be aliphatically saturated or unsaturated, or may be substituted hydrocarbon, having a polar or non-polar terminal substituent, which may be polar due to: 1) a charge, e.g., carboxylate, phosphate or ammonium; 2) zwitterion, e.g., betaine; or 3) a dipole, e.g., 2,4-dinitrophenyl, carboxylate ester, phosphate triester, etc.; or non-polar, such as thioether, silyl, halo, e.g., fluoro, selenyl, arsenyl, etc.

Where hydrocarbon groups are employed, particularly aliphatic groups of from about 6 to 24 carbon atoms, either saturated or unsaturated, a second layer may be employed to provide a bilayer membrane. Any lipids which provide a stable bilamellar membrane may be used for preparing the second layer. Alternatively, lipids forming stable lamellar membranes may be employed for both layers, avoiding covalent bonding to the surface. Illustrative groups include phospholipids, sphingomyelins, gangliosides, cholestric compounds, acylglycerols, acylcholines, and the like.

Conveniently, a polymerized lipid bilayer may be employed which may be prepared and positioned on the surface. See, for example, Wegner, Chapter V, R. P. Welch Foundation Conf. on Chemical Research XXVI Synthetic Polymers, Nov. 15–17, 1982, Houston, Tex., which disclosure is incorporated herein by reference. The degree of polymerization will generally be at least about 20% and may range up to 100% and may include an independent layer below the polymerized layer.

Various other materials may be used in conjunction with the surface, which materials may be bound either covalently or non-covalently or held mechanically in place adjacent to the surface. The materials may be naturally-occurring or synthetic or combinations thereof. These material include non-porous films, generally of from about 1 to 50 mil in thickness, normally being non-polar materials, such as polystyrenes, polyacrylamides, polyacrylates, polyolefins, e.g., polyethylene, polydienes, e.g., polybutadiane and polyisoprene, combinations thereof, etc. These layers may have independent integrity or rely on the semiconductor or insulative surface for support. They will be in contact, in whole or in part, with the semiconductor element, either directly or through intermediate layers.

These layers may have a passive role in providing for insulation or may play a more active role in being functionalized so as to interact or react with components of the sample. Thus, conjugated to the surface of the layers or internal to the layers may be a variety of compounds, particularly members of specific binding pairs, such as ligands and receptors. The thickness of the various insulative or coating layers on the semiconductor electrode surface proper will be less than about 2000 Å, usually less than about 1000 Å and frequently not exceeding about 500 Å.

The device may have a single continuous surface ranging from a surface area of about 1 mm$^2$ to about 250 cm$^2$, more usually about 25 cm$^2$, but in most instances will be a plurality of individual capacitive devices insulated from each other, so as to provide for independent signals to the same circuit. The individual units will generally range from about 0.1 mm$^2$ to 5 mm$^2$ or greater, the upper limit being primarily one of convenience, and the effect of size on sensitivity.

The individual units may be in contact with media which are partially or completely isolated from each other by the presence of partitions which allow for electrical communications, for example, membranes, porous walls or partitions extending only a partial distance to the surface, or insulated partitions which inhibit any electrical communication between the partitioned medium.

The surface of the capacitive device may be divided up physically in a variety of ways, providing for compartments, which may be of any convenient periphery, circular, square or the like, channels, which may be circular, serpentine or straight, or combinations thereof. Extended areas such as channels allows for inspection of a moving solution at different times. Channels can be provided by having grooves in the surface associated with the capacitive device and compartments can be divided by having indentations in the surface associated with the capacitive device. The number of independent units to be measured may be 2 or more, usually being 5 or more, and may be 50 or more, and could be as high as 500 or more.

As indicated above, the subject apparatus can address one or more incremental portions of one or more media to be analyzed, where the incremental portion or volume can be indicative of the gross properties of the medium or particular incremental portions of the medium, where properties of incremental portion may differ in their properties one from the other as well as from the properties of the gross medium. One can interrogate specific sites by having individual leads connected to an electrode associated with the specific site and energizing one of the electrodes and determining the capacitance or related electrical signal, which is affected by the incremental portion being assayed. In this way, one can address different portions of the medium to determine the state of the incremental portion as to a particular property and determine variations in the state of the medium over a large volume.

Furthermore, one can employ one or more channels and determine the state of the incremental portions along a channel, so that one can relate variations in the states of the incremental portions along the channel to a temporal change occurring in the medium. By using continuous or intermittent flow techniques, or by mixing two media which provide for a detectable reaction prior to entering the channel, one can provide a steady state at each capacitance site along the channel. In this manner, one can determine rates of reaction, by observing the steady state properties of the medium at different sites along a channel.

The counter- or second electrode will generally be positioned from about 0.01 mm to 5 cm distance from the insulative layer, more usually from about 0.1 mm to 10 mm. The counter electrode may be any conducting or semiconducting material, usually conducting material, such as metals, e.g., platinum; alloys, e.g. indium-tin-oxide; heavily doped semiconductive materials, e.g. silicon; conducting polymers, e.g. polypyrrole; or the like. The second electrode desirably will be of a material which is inert to the sample medium or will be coated with a protective layer, which may be a thin film, generally under about 5 mil, usually under about 1 mil, which may be an organic polymeric layer, a silicon oxide or nitride layer, or the like. Depending upon the semiconductive or first electrode, the second electrode will either be a continuous electrode facing the operating surface of the first electrode or a plurality of individual electrode electrically insulated from each other and associated with individual sites of the operating area of the first semiconductor electrode.

The second electrode or plate may assume a number of conformations. The second electrode may be a thin layer on a support, being present as stripes, dots or a continuous coating, may be a metallic or semiconductor layer or wafer.

Each of the individual capacitance electrodes or plates will be individually connected to a circuit, usually a common circuit, for detecting changes in capacitance or equivalent electrical measurement associated with the sample medium. Where a monolithic semiconductor wafer is employed having a plurality of electrode regions, each region will have its own lead to the circuit. This can be achieved in a variety of ways to be discussed subsequently.

The circuits employed for feeding an electrical signal to the capacitor will normally provide for a high frequency, generally greater than about 100 Hz, preferably greater than about 1000 Hz. The reason for the high frequency is as follows. Starting with a semiconductor electrode in the forward bias condition, the series capacitance of the two capacitors will be limited by the capacitance of the insulative layer. The capacitance of the space charge region (second capacitor) will be high due to the accumulation of majority charge carriers (electrons in n-type and holes in p-type semiconductors). As a reverse-bias potential is increasingly added, either by the external measurement circuit or by a change in the sample medium, the capacitance of the space charge region gradually falls to a minimum due to depletion of majority charge carriers in the semiconducting material at the semiconductor-insulative interface. Under this condition the series capacitance will be substantially limited by the space charge capacitance. With a small amplitude alternating voltage, the capacitance of this "space charge" remains substantially constant and unaffected by the alternating voltage provided by the capacitance measuring circuit.

Because current $(dq/dt) = C \, dv/dt$, where $dq$ is the charge flowing onto the capacitor, $C$, a small voltage change $dv$ will necessarily produce a small $dq$. However, it is more convenient to measure accurately large currents than small currents. Therefore, small values of $dt$ (high frequency) will provide the desired large currents for any given value of $C$ and $dv$. In other words, the impedance, $Z$, of a capacitive circuit is $1/j\omega C$, where $\omega = 2\pi f$, with $f$ being the frequency. Applying Ohm's law generalized for complex impedance it can be seen that high frequencies reduce the impedance and thus increase the current for a given voltage change. Thus, the measured current, for any given alternating voltage amplitude and any given electrode capacitance, will be proportional to the frequency. Therefore, at high oscillating voltage frequencies, the capacitance will be more easily measured by an external current measuring circuit. The frequency, however, must not be so high as to exceed $\tfrac{1}{4}RC$, where $R$ is the total series resistance of the circuit employed in measuring the capacitance $C$. This RC time constant limits the speed of response of the circuit to a change in $dv/dt$. (See for example, pp 11-15 of Bard and Faulkner, supra).

The region of applied DC potential employed for the measurement will be at or near (within about $\pm 2$ volts) the potential at which the semiconductor is neither forward nor reverse biased (the "flat-band" potential). It is found that the rate of change of capacitance in relation to the rate of change in the DC applied potential is largest, when the circuit is operated at or near the flat-band potential of the semiconductor. Provided that the surface potential, developed at the (first) semiconductor and (second) counter electrode change differently as a result of a change in the composition or concentration of analyte, there will be a correlated shift in the measured flat-band potential compared to the absence of analyte and the circuit can provide for measuring the magnitude of that shift.

Various circuits will be described which can be employed for capacitance or related electrical measurement. In one mode a bias potential of known magnitude is added back to keep the measured capacitance exactly constant. The magnitude of this added potential will be governed by the change in potential caused by the change in analyte. Therefore, the added potential will be directly related tot he magnitude of the change in analyte concentration, which can be calibrated with standards of known concentrations of analyte.

Alternatively, one could have the circuit operate at a constant bias potential and relate changes in capacitance (at this potential) to changes in analyte concentration. This technique suffers from the disadvantage of having less sensitivity, since the change in capacitance with change is applied potential becomes smaller as the surface potential moves away from the flat-band potential. Thus, there is a limited range of analyte concentrations which can be measured at maximum sensitivity.

The subject device can be used to measure a wide variety of analytes involving various detection systems and labels. For example, the subject device can be used for measuring rates of reaction, such as enzymatic reactions, where the enzymatic reaction results in a change in the ionic strength of the medium, for example, changes in pH, changes in number of charged species, or the like. This can be done in a dynamic or static way, for example, by employing a moving stream, one can make the rate determination substantially instantaneously. Alternatively, by having a relative static solution at a particular site, where the electrode is energized intermittently, readings can be taken at different times and the rate determined.

The subject method also can be used with semi-solid or solid media, employing appropriate adaptations. For example, gels can be used, where the migrating species provides for a change in surface potential. Thus, one can detect the presence of nucleic acids, proteins, saccharides, or the like, where the compound provides for the desired changed in surface potential. Examples of such situations involve electrophoresis, isoelectric focusing, or the like.

Of particular interest will be the use of the subject invention in detecting the presence of a specific component of a medium, where the component may be a chemical, either synthetic or naturally-occurring, such as drugs, hormones, proteins, steroids, receptors, nucleic acids, or the like; or aggregation of chemicals, such as nucleosomes, viruses, cells, both prokaryotic and eukaryotic, or the like. These determinations will frequently be made in physiological fluids, such as blood, plasma, saliva, cerebral spinal fluid, lymph, urine, or the like.

The determinations will involve a combination of a ligand and receptor, where the ligand and receptor have a specific affinity, one for the other, so that they provide a pair of specific binding members. Receptors for the most part will be antibodies, enzymes, or naturally-occurring receptors and can for the purposes of this invention include nucleic acids, while ligands may be any compound for which a receptor is available or can be made.

For the homogeneous system, it will only be necessary that binding result in modulation of an assay system which results in modulation of the capacitance or related electrical signal. Thus, by having enzymes as a label, which catalyze a reaction which results in a substantial change in pH or ionic strength, the rae of change can be related to the amount of analyte, where binding of specific binding members results in a change in enzyme activity. Assays of interest are described in U.S. Pat. Nos. 3,817,837, 4,208,479, 4,275,149 and 4,341,865. These patents involve enzymes, compounds which interact with enzymes, and particles.

With heterogeneous systems, separation between complexes of specific binding pair members and uncomplexed specific binding pair members can be achieved. This is achieved by having one of the members of the specific binding pair bound to a solid surface. One could have antibodies bound to the solid surface and could employ a sandwich assay which involves the antigen as the analyte and a second labelled antibody which would bind to any antigen bound to the antibody bound to the surface. By employing appropriate labels such as enzymes, one could detect the presence of the antigen by a change in the capacitance at a capacitor site. Descriptions of heterogeneous techniques involving enzymes may be found in U.S. Pat. Nos. 3,654,090, 3,791,932, and 4,134,792.

If one wished to use repeatedly the same surface, one could apply a member of a specific binding pair to the surface, where the complementary member is conjugated to a member of a specific binding pair related to the analyte. For example, one could coat the surface with the same or different sugars, haptens, receptors, antibodies, or members of naturally occurring ligand-receptor pairs. One would then conjugate the member of the specific binding pair related to the analyte to the binding member complementary to the material bound to the surface. To illustrate, one could coat the surface with a saccharide and conjugate the analyte related specific binding pair member, e.g., antigen, to a lectin. Thus, one could prepare conjugates of antibodies to a protein analyte and lectins. By adding a solution of the antibody-lectin conjugate to the saccharide-coated surface, the antibodies would become bound to the surface. One could then carry out the assay as described above and after completing the assay, remove the complexed material from the surface by adding a concentrated solution of the saccharide. One can use other pair by analogy, where in place of a lectin, an antibody or natural receptor could be employed. Thus, a single surface can be used which could be repetitively replenished, so that the same or different types of assays may be employed after each determination. By binding different compounds to the surface at different sites, one can direct specific binding pair members to a specific site with the appropriate conjugate.

Various techniques may be used with enzymes for amplification and enhanced sensitivity. pH cascades can be employed, by employing enzymes having different pH optima. By having the bulk solution at a pH for a pH-insensitive enzyme, which produces a product which can provide a different pH in a localized environment, which is the optimum for a second enzyme, which produces a product which further changes the pH in the same direction, one can provide for localized enhancement or amplification.

In may situations it will be of interest to determine the presence of a natural receptor in a physiological fluid, particularly blood or plasma. Usually, the receptor will be an antibody, resulting from an autoimmune disease, foreign substance, or an infection. The antibody may be detected in a competition assay, where the endogenous antibody compete with labeled antibody for the complementary antigen or the antibody may serve as a bridge to bind labeled antigen to antigen bound to a surface or particle. Otherwise, for the most part, the antibody assay would follow the techniques employed for detecting antigens.

In some situations it may be desirable to have lipid membranes composed of monolayers, bilayers, or multilayers covalently or non-covalently bound to the semiconductor electrode surface or other surface which can be brought in proximity to the electrode surface. A single lipid layer may be formed by employing aliphatic silyl halides or esters, where the silyl compound may have from one to three aliphatic chains, generally of from about 12 to 24 carbon atoms, more usually of from about 12 to 20 carbon atoms. In addition, other materials may be present, either bonded to a silyl group or bonded to the aliphatic chain, including aryl groups, functionalities, e.g., carboxyl groups, halo groups, amino groups, or the like. One can then provide for the second layer by dipping the surface through a lipid monolayer, formed for example at an air-water interface, so that the second layer forms on the first layer to form a bilayer. Multilayers may be formed subsequently by withdrawal of the bilayer coated surface through the lipid monolayer followed by repeated dipping steps to deposit the number of layers desired.

A wide variety of lamellar-forming lipids may be employed, particularly phospholipids used in the formation of liposomes and the like. Alternatively, a bilayer may be formed by plasma cleaning of the particular surface, passing the wafer vertically through the monolayer and pulling the wafer out at a speed slow enough to permit water to drain from the surface. The wafer is then pushed through the monolayer horizontally, followed by covering with a cover slip. Lipid multilayers, may be formed by repetitious deposition of lipid monolayers, or lipid bilayers or combinations of the two.

The bilayers allow for lateral diffusion within the layer. One can provide for various groups bound to lipids which will specifically bind to an analyte, e.g., antibodies. One could provide for ionophores as labels, where the ionophores allow for transports of ions through the bilayer to the electrode surface. Thus, ionophores may be coupled to specific binding partners, e.g., ligands or receptors which would specifically bind to their complementary partner bound to the bilayer. The presence of the free ionophore would modulate the measured capacitance as indicated below. Illustrative ionophores include mellitin, nonactin, valinomycin, alamethicin, crown ethers, and the like.

Ionophores and ion channels increase ionic conductivity through lipid membranes. This increase in conductivity may be monitored by a change in capacitance of an underlying semiconductor electrode by one of several principles, three of which are given below by way of example. By the first principle, a substantial difference in ionic composition is established across the lipid membrane by trapping a reservoir of ions between the membrane and the insulator of the semiconductor electrode. The trapped ions must be of at least two separate types, such as, calcium and sulfate ions, potassium and chloride ions, sodium and fluoride ions, etc. The ions may be trapped either in the form of a solution, in the form of a precipitate, or bound to an ion-exchange resin or polymer. When the lipid-membrane-coated semiconductor electrode is bathed in an electrolyte medium, a substantial electrical potential will develop across the lipid membrane. The magnitude of this potential can be calculated from the well-known Goldman equation (See for example, G. Zubay, Ed., *Biochemistry,* Addison-Wesley, 1983, Menlo Park, Calif., p. 1148). Accordingly, the concentration of each ionic species on each site of the membrane, the charge of each ion and the relative permeability of each ion through the membrane will determine the magnitude of the electrical potential drop ($\Delta\psi$) across the membrane.

As ionophores may differentially affect the permeability of the membrane to various ions, $\Delta\psi$ will vary with the activity of ionophores within the membrane and with the formation of ion channels by, for example, membrane receptors. Because $\Delta\psi$ is a voltage which is internally applied across the semiconductor electrode and is in series with the externally applied DC bias potential, a change in $\Delta\psi$ will cause a shift in the capacitance of the semiconductor electrode identical in magnitude to that caused by an equivalent change in DC bias potential. This capacitance change may be measured directly. Alternatively, an offsetting DC bias potential may be applied in order to return the capacitance to its exact starting value and the magnitude of this offsetting DC bias potential recorded. Several means for measuring either the change in capacitance or the change in DC bias potential have been described above.

A second principle whereby the activity of membrane ionophores can be measured is by applying step changes in the DC bias potential and monitoring the effective capacitance as a function of time after the step change in DC bias potential. To further explain this method, when the insulator on the semiconductor has surface ionizable chemical groups (such as hydroxyls, amines, carboxyls, sulfhydryls, imidazole, guanidino, or the like), binding and unbinding of protons to the ionizable groups will result in a change in the surface potential of the insulator that can be monitored by a change in capacitance of the semiconductor electrode, as mentioned previously. A step change in the DC bias potential will result in the binding or release of protons to the insulator surface, depending on the sign of the DC bias potential step. Introduction of a membrane immediately adjacent to the insulator will tend to impede the movement of hydrogen ions to and from the surface. Thus, the pH in the region between the bilayer and the insulator will be affected by the proton flux through the membrane which in turn is affected by the number of and activity of proton-carrying ionophores in the membrane. If the membrane increases its permeability to hydrogen ions, then the rates of change in capacitance will increase for a given magnitude of step change in DC bias potential. By varying the frequency of step changes in DC bias potential, a wide range in rates of capacitance change may be measured. Therefore, a wide range of hydrogen ion permeabilities may be monitored.

A third principle which may be utilized to measure ionophore activity is the establishment of a potential difference across the lipid bilayer by a temporal change in the ionic composition of the medium on the liquid medium site of the membrane (opposite side from the semiconductor electrode). Either a sudden step or a gradual change in the activity of at least one ion in the liquid medium will produce a potential difference across the lipid membrane. The exact magnitude of this potential again may be calculated from the Goldman equation, as mentioned previously. As time passes following the change in ionic composition, ions will redistribute across the lipid bilayer and the potential difference that was generated will be dissipated. Ionophores capable of carrying ions across the lipid membrane will affect the rate at which the potential difference is dissipated. Also, the initial potential measured after the change in ionic composition will be affected by such ionophores because of their effect on the permeability term(s) in the Goldman equation. Either this initial effect, or the dissipation (relaxation) rate may be measured by the capacitance techniques mentioned previously, and then related to ionophore activity.

Besides haptens, proteins and saccharides, nucleic acid can also be detected by the subject method. Nucleic acids, either RNA or DNA, can be detected by hybridization with probes having complementary sequences in a competitive or non-competitive manner. In a competitive manner, a nucleic acid sequence may be bound to a surface. A sample suspected of containing the complementary sequence may be combined with a labeled complementary sequence, e.g., labeled with biotin. The mixture is then combined with the surface bound polynucleotide under hybridization conditions and non-specifically bound oligonucleotides removed. Enzyme-avidin conjugate may then be added, where the avidin binds to any biotin present. The presence of specifically bound enzyme may then be detected in accordance with the ways described previously.

Microorganisms can also be determined, particularly bacteria, where the growth of the bacteria results in a change in pH. Thus, one can dissolve a sample in a nutrient medium and monitor the change in pH of the medium with time, where a change in pH indicates the presence of an organism. One can modify the situation by using nutrient media which are specific for the growth of certain organisms or which provide for changes in pH with specific organisms or determine the sensitivity to various antibiotics by employing, for example, two media, one with and one without the antibiotic and determining the rate of change with pH. Thus, by employing a plurality of samples containing different additives, one can obtain information about the nature of the organism and its response to various biostats or biocides, such as antibiotics.

The devices according to the present invention may be fabricated in a variety of ways to do a multiplicity of measurements, depending on whether individual leads are directed to individual pixels in the semiconductor (first) electrode or individual plates of the counter (second) electrode. Where individual pixels are present in the first electrode, various techniques may be used to isolate the individual pixels and direct leads to each of the pixels.

In one embodiment the main body of the first electrode is lightly doped and subsequently oppositely doped by diffusion in the regions surrounding each pixel. The surfaces could then be insulated by initial thermal oxidation in oxygen at temperatures in the range of 500° to 1200° C. to provide a thickness of about 100 to 1500 Å. A silicon nitride film can then be chemically vapor deposited using ammonia and $SiH_4$, $SiCl_4$, or $SiH_2Cl_2$ at temperatures in the range of about 500° to 1000° C. for a thickness of about 500 to 1500 Å to provide an insulative layer of about 600 to 2000 Å. The wafer may then be annealed in an inert or reducing atmosphere such as argon or nitrogen, or hydrogen, respectively. The wafer may then be etched on the reverse side to expose the doped regions. The reverse side may then be plated with a patterned metal conductor to provide separate individual contacts with each of the doped regions. Aluminum could be used for both the doping and the metal contact. Isolation of pixels can also be achieved by etching a doped silicon wafer at a plurality of sites so as to define a number of small bowls. The bowls may then be filled in epitaxially with silicon and oppositely doped from the surrounding region. The surfaces then may be insulated, etched, and pattern metallized as mentioned above to separately connect each of the expitaxially grown pixel regions.

An alternatively and preferred method is to employ a very thin doped silicon wafer and to implant opposite dopant as ion implantation techniques into the regions surrounding each pixel (but not into the pixel regions). The wafer may be annealed at high temperature to remove crystal defects in the implanted regions or these defects may be allowed to remain so they tend to make the region nonconducting. The wafer may then be coated with insulating layers, selectively etched, and pattern metallized, as indicated above, to provide for separate external connections to each of the pixels.

Other fabricating techniques may also be employed, as appropriate.

Both the bulk of the monolithic semiconductor 12 and the pixel regions 20 of FIG. 1 generally will be doped to about $10^{14}$ to $10^{17}$ atoms/cc. Regions 12 and 20 may be either similarly or oppositely doped. When they are similarly doped there will be an oppositely doped region, 17 of FIG. 2A, separating each of them one from another. Oppositely doped regions generally will be doped from about $5 \times 10^{14}$ to $10^{17}$ atoms/cc. An insulative surface coating, 22, for example silicon oxide, silicon nitride, or a composite thereof, is present to insulate the semiconductor electrode from any fluid in channel 16 and provides for a dielectric material which provides a substantially constant capacitance in series with the variable semiconductor capacitance. Non-diffusibly bound to the surface of the coating 22, in close proximity to some of the pixels, are specific binding compounds 24, indicated as small hairs, which serve to bind to complementary members, for example receptors and ligands, e.g., antibodies and antigens.

The channel can be quite small. Generally the space between the two plates 12 and 14 is from about 0.01 mm to 50 mm, and more usually is from about 0.1 mm to 10 mm. The width of the channel will generally be from about 0.1 mm to 100 mm, and more usually from about 0.1 mm to 10 mm, so that the cross-section will generally be in the range from about $10^{-4}$ mm$^2$ to 5000 mm$^2$, more usually from about $10^{-2}$ mm$^2$ to 100 mm$^2$. The electrode, 14 and pixels 20, with the conductive fluid in the channel provide individual capacitive elements which allow for individual measurements of discrete portions of the assay medium. Each of the pixels 20 is connected by an independent lead 26 to a switching circuit 30 which serves to connect each of the pixels individually to the circuit for a measurement of capacitance or related electrical property. In some instance it may be of some interest to measure the electrical signal from more than one pixel simultaneously, where one wishes to obtain an averaged or combined value. Various switching circuit components such as field-effect-transistor logic arrays are commercially available to accomplish this task. In addition to the switching circuit, the circuit includes a voltage oscillator 32, a variable DC voltage generator 34 and an AC ammeter 36. Voltage oscillator 32 applies an oscillating voltage signal of set amplitude and frequency across electrode 14 and a single pixel 20. The alternating current through electrodes 14 and pixel 20 is proportional to the capacitance, as discussed above, and is measured by ammeter 36. After measurement at one pixel, the result is recorded and the switching circuit 30 switches to another pixel where the above process is repeated. DC voltage generator 34 is only used for a constant DC bias potential in this method. The value of this constant DC bias potential is chosen at the outset of the measurement to substantially maximize the change in capacitance observed with small changes in measured analyte.

A second measurement method uses DC voltage generator 34 to maintain a constant capacitance by imposing a variable DC bias voltage which alters the space charge region 25 of an electrode (pixel) 20, Thus, the capacitance change resulting from a characteristic of the medium, e.g. a pH change, caused either by a chemical reaction (in the medium or by addition of a substantially different medium) is offset by the DC voltage applied by generator 34. The amount of DC voltage applied can be measured and will be proportional to the change that has occurred in the medium.

Figure 6:
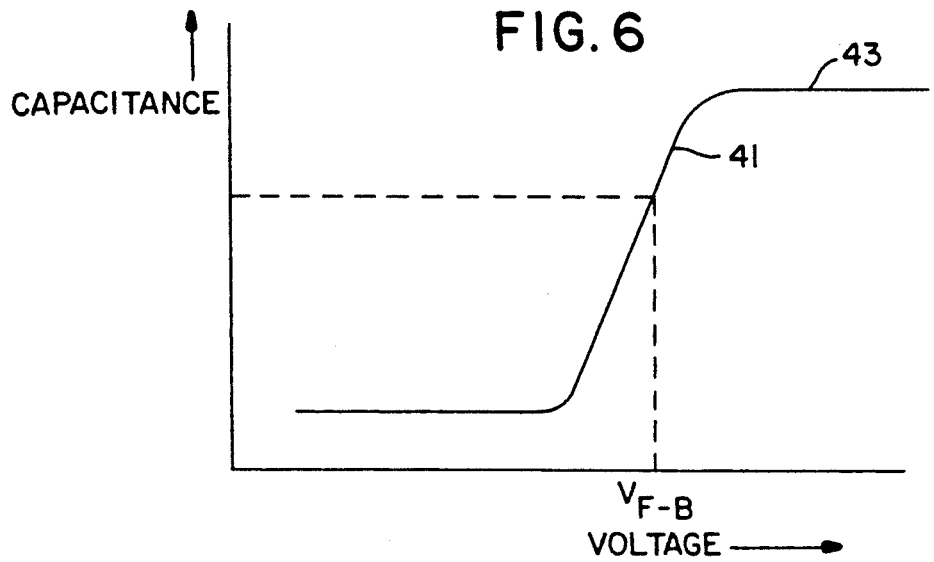
FIG. 6 is a graph of capacitance measured with high frequency (>100 Hz) voltage oscillations vs. applied voltage for an embodiment of the invention.

The reason for using this second method can be seen by referring to FIG. 6. A plot capacitance measured at high frequency versus DC voltage is shown. As a chemical reaction proceeds to change the pH, for example, the capacitance will increase until it is out of the region of maximal slope 41 and into region 43 where capacitance is only slightly affected by a change in DC voltage. At this point, a change as a result of further chemical reaction will no longer cause a measurable increase in capacitance. In order to be above to measure this change, a reverse bias is applied to bring the capacitance back into the sensitive region 41, preferably to flat-band potential, $V_{F-B}$.

The reverse bias is applied by using DC voltage generator 34 to superimpose a DC voltage on the AC signal from voltage oscillator 32 in FIG. 1. Feedback is provided by rectifier 45 which rectifies the AC signal and filter 47 which converts the rectified AC voltage into a DC voltage. DC voltage generator 34 respond to the DC voltage of the filter 47 and will produce a voltage to keep the rectified AC voltage constant. The amount of chemical activity will be proportional to the voltage applied by DC generator 34, and can be read with voltmeter 49.

The current through counter electrode 14 can cause the surface of this electrode to become polarized, introducing error into the voltage measurement. The amount of polarization will depend upon the material used for electrode 14 and the solution present in channel 16. Reference electrode 37 may be used to give a true reading of the voltage. The potential at electrode 37 is measured by a high impedance input of voltmeter 49 and thus draws an insignificant amount of current so it will not become polarized.

Figure 2A:
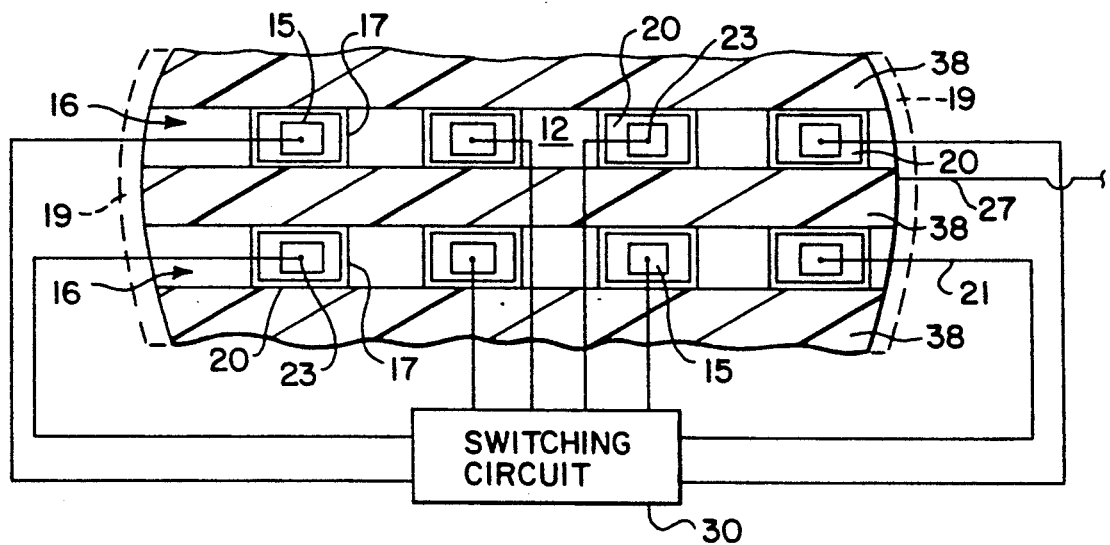
FIGS. 2A and 2B are top and side views of a modified embodiment of FIG. 1.
Figure 2B:
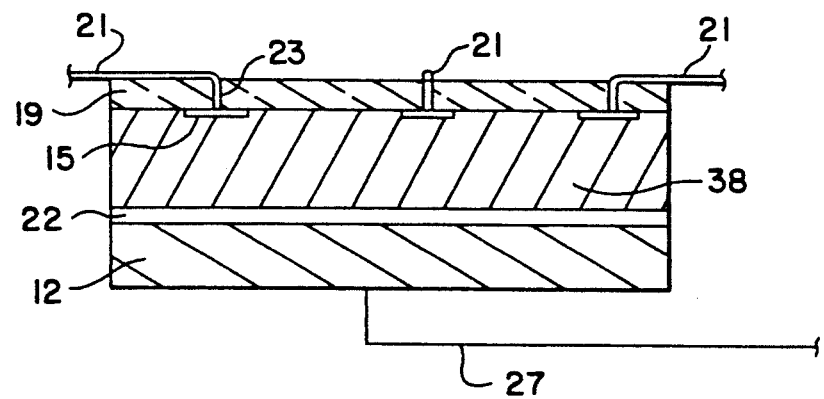

In FIG. 2A, a top view of a two-channel modified embodiment of the device of FIG. 1 is indicated, while FIG. 2B shows a side view. Pixels 20 are separated by the monolithic semiconductor substrate 12, each pixel being junctionally isolated by oppositely doped borders 17 from every other pixel 20. As for the device of FIG. 1, an insulative layer 22 provides for a high electrical resistance between semiconductor electrode 12 and the conductive medium in channels 16. As in the case for the device in FIG. 1, the insulative layer 22 is sufficiently thin, however, to allow substantial capacitance between the conductive medium and the semiconductor electrode. Adjacent to the insulative layer 22 on the semiconductor electrode, each channel 16 is bordered by barriers 38 which prevent mixing between the channels, and which can serve as inert dielectric separators between electrode 12 and counter electrode 14 of FIG. 1. As appropriate, the barriers may be functionalized to serve in binding specific binding members, providing a local source of a particular chemical or composition, e.g., enzymes, or the like.

As shown in FIG. 2A, electrode 14 of FIG. 1 may be segmented so as to have individual electrode plates 15, each plate individually isolated from the other and individually connected to an external circuit and immediately opposite the pixels 20, where the pixels, while not requiring electrical insulation one from another, are preferably electrically insulated from each other. In other words, individual pixels need not be formed and substrate 12 then acts as a single, large electrode.

In this embodiment, the channels 16 are very shallow or narrow or a combination of shallow and narrow so that when the individual electrode plates 15 are spaced apart, there will be minimally conducting connection between two individual counter electrode plates 15. Alternatively, insulative barriers may be placed in the channels 16 so as to further limit the conductance between the individual counter electrode plates 15. The circuit employed with this embodiment can be substantially the same circuit which is employed where only the pixels 20 are electrically insulated. As an oscillating voltage signal is applied to each individual electrode plate 15 from switching circuit 30 through leads 21, the capacitance at a localized portion of semiconductor 12 is measured. Other sites are negligibly affected due to the low conductance of the channels between sites.

In FIG. 2A individual electrodes 15 are mounted on a transparent nonconducting support plate 19 indicated by the broken lines. Leads 21 painted on the opposite side of plate 19 make contact with the electrodes 15 at point connector 23. In FIG. 2B a side view of the device of FIG. 2A is shown, indicating how support plate 19 supports electrodes 15 and leads 21 opposite the monolithic semiconductor 12. Since individual pixels are not required, a single lead 27 in ohmic contact with semiconductor 12 leads to the external measurement circuitry. In this embodiment, lead 27 from the semiconductor electrode 12 may be connected, for example, to the AC ammeter (shown in FIG. 1); leads 21 from the individual counter electrode plates 15 are connected to the switching circuit 30 shown in FIG. 1. Thus, this embodiment includes the case where the connections to the electrical circuit for measurement of capacitance of the counter electrode 14 and semiconductor electrode 12 are reversed.

The embodiments of FIGS. 1, 2A, and 2B can be expanded to include a large number of channels 16. Alternatively, individual wells could be used rather than channels, with each pixel 20 or plate 15 placed opposite to, or in contact with liquid medium in a separate well.

Returning to FIG. 1, the leads 26 are connected to the pixels 20 by ohmic contact, for example by depositing the appropriate metal and diffusing the metal into the pixel regions 20. The individual leads 26 may make ohmic contact on the opposite side of electrode 12 from channel 16. Alternatively, the leads 26 may be brought in on the same side as the channel 16 and subsequently covered over with the insulator 22 or an overlaying insulator in order to insulate the leads from the fluid in the channel. The former method is preferred over the latter because the leads on the opposite side of the channel are less prone to electrical short circuits.

In carrying out the assay, fluid will be introduced into the channels 16, where the fluid might have one or more analytes and one or more of the channels may serve as standards, where known amounts of the one or more analytes would be present. The fluid would be allowed to flow into and fill the channel and could then be stopped.

Where there are specific binding members 24 bound to the surface 22, the complementary members of the specific binding pair would bind to those specific binding members. For example, if the specific binding member is a surface protein of a microorganism, the microorganism would bind at that site.

If microorganisms are involved in the assay, by employing a nutrient medium for the microorganisms, they will metabolize nutrients and produce a change in pH. The resulting change in pH will result in a change in the measured capacitance. The magnitude of the added potential necessary to maintain a constant capacitance will be directly related to the magnitude of the change in the pH and this change can be related to the number of organisms present at that site. By alternating sites having antibodies and lacking antibodies, one can compare the different sites, so that a background value can be determined and directly subtracted from the value observed at a site having antibodies.

By employing switching circuit 30, each one of the pixels can be addressed and the capacitance of that site determined while maintaining a constant potential at the counter or reference electrodes 14 and 37, respectively. Alternating, instead of maintaining constant potential, the external measurement circuit could automatically provide for a return to a defined capacitance value by adjusting the DC voltage applied. The potential required to return the capacitance to the defined value could be recorded during the period of connection of each individual pixel region to the external measurement circuit (via switching circuit 30).

Figure 3A:
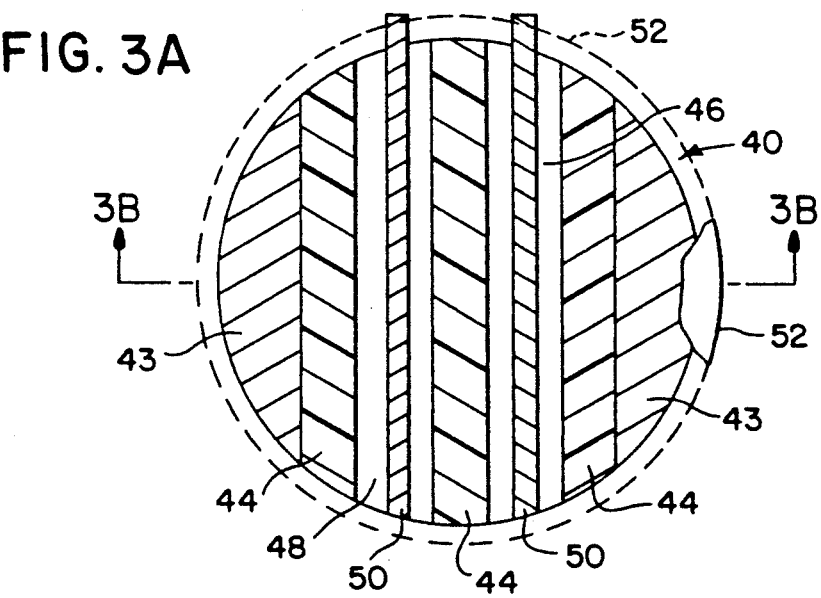
FIGS. 3(A) and (B) are top and cross-sectional views of an embodiment of a channel device.
Figure 3B:
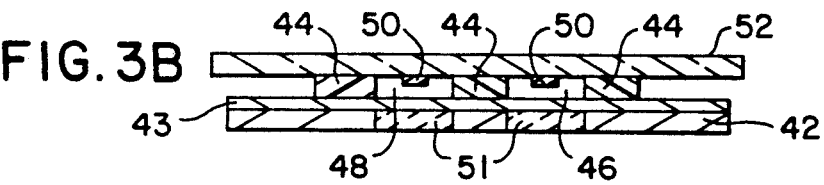

Another embodiment is depicted in the top view in FIG. 3A and in side view in FIG. 3B. This embodiment similarly employs channels. The device 40 has a first electrode 42 which is a semiconductor having a thin insulative layer 43 shown partially cutaway, and is one of a two or multiple electrode system. Insulative spacers 44 define channels 46 and 48. Controlling electrodes 50, which may be of any convenient conducting material, such as platinum, indium-tin oxide, polyvinyl pyrrole, or the like, extend the length of the channel and would be in contact with the medium in the channel. The controlling electrodes 50 may be coated as a thin strip onto the surface of a plastic or ceramic plate 52 which is supported by spacers 44. The supporting plate serves to enclose the channel. As in the case of the device in FIG. 1, the first electrode 42 would have an insulative layer coating 43 on its surface that acts as a dielectric. The first electrode 42, in addition, has individual junctionally isolated regions 51 below the insulative layer. The junctionally isolated pixel regions could extend the entire length of the channel so that a single reading would be obtained for each channel which would be indicative of the properties of the medium in each channel. By having a standard medium in one channel and the sample medium in the other channel, the differences between the two channels could be detected as indicative of the amount of analyte in the sample medium.

Figure 4A:
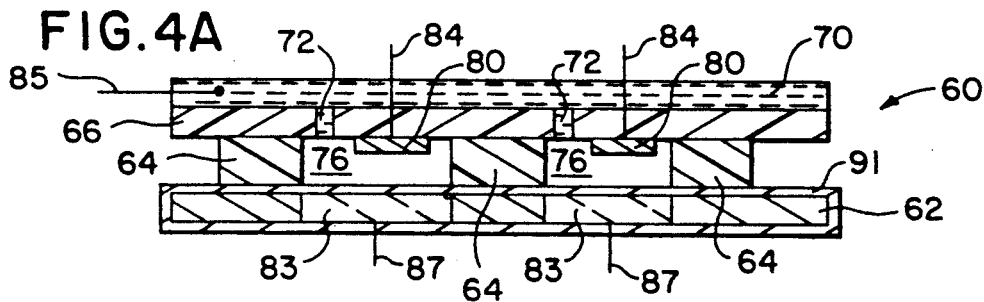
FIGS. 4(A), (B) and (C) are cross-sectional views of alternate embodiments of the invention.
Figure 4B:
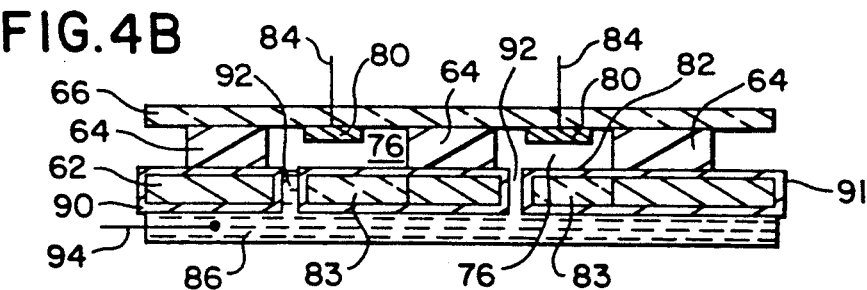
Figure 4C:
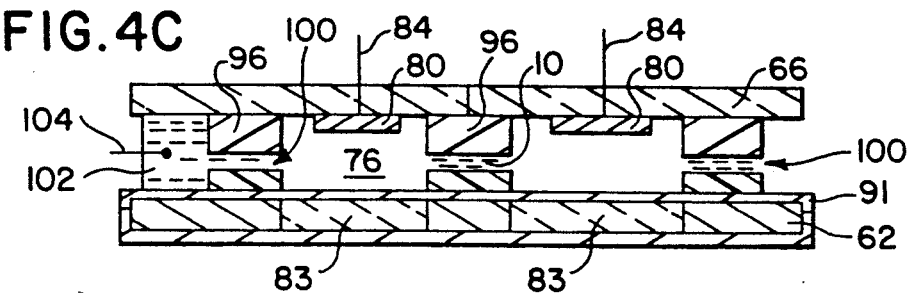

In FIGS. 4A, 4B, and 4C, alternative embodiments are shown which accommodate a reference electrode. In FIG. 4A, the device 60 has a first semiconductor electrode 62 which is a monolithic doped semiconductor coated with insulation layer 91. Spacers 64 support inert plate 66 upon which is coated a reference electrode gel 70. Plate 66 has holes 72 which are filled with a reference electrode gel 70 or allowed to fill with sample medium which provide electrical communication between the reference electrode gel 70 and the conductive assay medium in the channels 76. The counter electrode or controlling electrode 80, which can be any inert conducting material, is coated onto the inert plate 66 so as to have contact with the assay medium. Each of the counter electrodes are either independently or jointly wired through insulated leads 84 to an external circuit (not shown). Lead 85 provides for electrical contact with the circuit about the reference electrode gel 70.

Semiconductor regions 83 are oppositely doped from the monolithic semiconductor electrode 62, so as to create a p-n junction for junctional isolation at the interface between the oppositely doped region 83 and the bulk of the semiconductor wafer 62. Leads 87 individually connect the oppositely doped pixel regions to an external circuit (not shown).

An alternative embodiment is found in FIG. 4B where the reference electrode gel 86 is separated from the semiconductor electrode 62 by means of an insulation layer 90. This insulation layer may be either the same or substantially different from the insulative layer 91 separating the semiconductor electrode from the medium in the channel. Where they are identical, the semiconductor electrode may be first cut (or deposited) in the desired shape, next the holes 92 drilled, and then the insulative layer 90 and 91 deposited. It is important to note that the insulative layer must in all cases extend through the holes 92 so that there is no short circuit between the semiconductor electrode 62 and the medium in the channels 76. Holes 92 in the semiconductor electrode 62 are filled with the reference electrode gel 86 or allowed to fill with sample medium, so as to provide for electrical communication with channel 76 and reference electrode gel 86. Lead 94 provides for electrical connection to the reference electrode gel 86. Other features of the embodiment are similar to those shown in FIG. 4A.

In a third embodiment, depicted in FIG. 4C, the spacers 96 have holes 100 which are filled either with reference electrode gel 102 or allowed to fill with sample medium so as to allow electrical contact between the reference electrical gel and the sample medium in each of the channels 76. Lead 104 connects the reference gel 102 to an external circuit. In this manner, a reference electrode is in electrical communication with the channels 76. Other features of the embodiment are similar to those shown in FIG. 4A.

In employing the above embodiments, sample or control media would be introduced into the individual channels. Each channel could have each lead 84 from individual controlling electrodes 50 and 80 connected independently to a switching circuit so that potential could be individually applied to each of the controlling electrodes. Alternatively, in the embodiments depicted all channels could have common controlling electrode 50 and 80, in which case the individual pixel regions 51 or 83 in the semiconductor electrode 42 or 62 must be individually connected to a switching circuit, so that, in any case, a potential may be individually applied between an individual pixel region 51 or 83 and the controlling electrode 50 or 80 so as to measure separately the series capacitance between the controlling electrodes 50 or 80 and each pixel region 51 or 83 in the semiconductor electrode 42 or 62 independently.

The medium present in a channel 46, 48, or 76 would affect the surface potential of the insulator 43 or 91 situated between the medium and semiconductor electrode 42 or 62, respectively. Thus, the flat band potential (and therefore the capacitance) of the semiconductor electrode will vary with the nature of the medium in the channel. By applying a fixed DC potential to the controlling electrode and measuring the magnitude of an added DC bias potential necessary to return the capacitance to a predetermined value related to the flat-band potential of the semiconductor as discussed above, the observed bias potential may be related to a characteristic of the medium, for example, pH, $Na^+$ and $K^+$ concentration, etc. By comparison of the bias potential observed with the sample medium with respect to the bias potential when the channel contains a standard medium, the property of interest in the sample medium may be determined.

Specific ions such as $Na^+$, $K^+$, $Ca^{++}$, $Li^+$, $Cl^-$, $F^-$, or the like may be selectively sensed at selective pixels by overlaying said pixels individually with membranes having incorporated selective binding molecules, such molecules selectively binding $Na^+$, $K^+$, $Ca^{++}$, etc. Selective and differentials binding of ion species to the membranes at individual pixel sites leads to establishment of potentials (voltage differences) at the membrane-medium interface which are dependent on the concentration of the selected ionic species in the adjacent conductive medium. Because the local potential established at the membrane-medium interface is in series with the applied DC bias potential, the voltage dependent capacitance of the space charge layer in the subjacent (pixel) region(s) of the semiconductor electrode will be affected by the binding of the selected ionic species to the membrane in these regions. Either the magnitude of the change in capacitance, or the magnitude of the shift in DC bias potential required to maintain constant capacitance, may be measured by external circuitry, as described previously.

Figure 5:
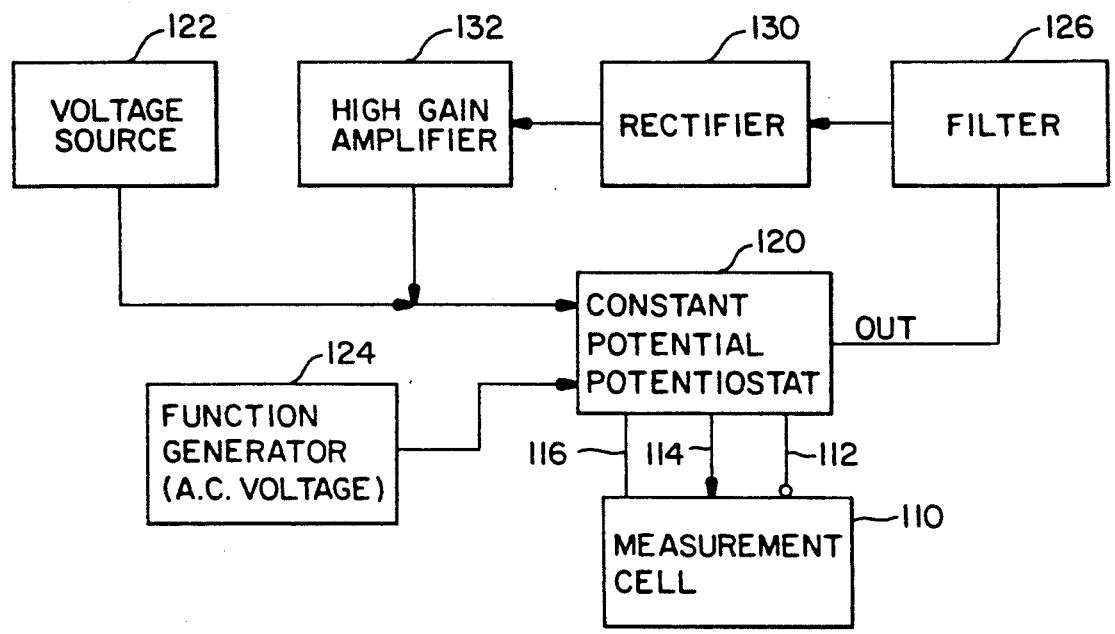
FIG. 5 is a block diagram of an embodiment of a circuit for a capacitance detector operated in constant capacitance mode.

A circuit which may be used with the above devices is depicted in FIG. 5. In FIG 5, a measurement cell 110 could be any of the previous embodiments which have been described. In electrical communication with the measurement cell is a lead 112 (or multiplicity of leads together with a switching circuitry as discussed above) to the pixel regions in the semiconductor (working) electrode. Also in communication with the measurement cell is a lead 114 to the reference electrode, and a lead 116 (or multiplicity of leads together with a switching circuitry as discussed above) to the controlling electrode(s). All leads are appropriately connected to a constant potential pentenitostat 120. A constant voltage source 122 is connected to the constant potential potentiostat to provide a fixed DC potential. This fixed potential insures that the initial voltage in the measurement cell is near the flat-band voltage. A function generator 124 is also connected to the input side of the potentiostat 120 is also connected to the input side of the potentiostat 120 to supply an AC voltage for measuring the capacitance between working electrode lead 112 and controlling electrode lead 116.

The fixed potential from voltage source 112 is applied across leads 112 and 114 by potentiostat 120 along with the AC voltage from function generator 124. The proper voltage across these leads is obtained by supplying a current through the controlling electrode lead 116. The resultant alternating current that passes through leads 112 and 116 is converted to a voltage and fed to a bandpass filter 126 to remove the DC voltage and any high frequency noise. The remaining AC signal is rectified by rectifier 130 and then amplified by amplifier 132 to provide a feedback potential which is added to the fixed potential from the voltage source 122 and then led to potentiostat 120. Changes in the medium in the measurement cell will cause the capacitance between leads 112 and 116, and thus the current, to vary. The current feedback signal will cause potentiostat 120 to apply a bias DC voltage to keep the AC signal constant, as described above. By measuring the increase or decrease in DC bias potential added to the circuit by the potentiostat 120 to maintain a constant AC signal as a result of changes in the medium in the measurement cell, the observed DC bias potential would relate to a characteristic of the medium.

For example, if one was interested in a pH change, and when employing a surface capable of a Nernstian and selective response to pH, for each change in a single unit of pH in the medium one would observe a change of about 59 mv in DC bias potential at 23° C. Therefore, employing a system where the presence of the analyte results in a pH change, one could detect the presence of the analyte by observing a change in the DC bias voltage provided by the potentiostat 120.

In accordance with the subject invention, novel methods and devices are provided for rapid and accurate detection of a wide variety of analytes or changes in a medium which will affect a capacitance or related electrical signal. These devices allow for substantially simultaneous determination of a large number of analytes in a particular medium or analytes in a variety of samples. By employing a variety of protocols with different reagents, products can be produced which greatly amplify the effect of a particular analyte in changing a capacitance or related electrical signal. The subject devices can be fabricated readily from available materials, may use reagents which are presently available or can be easily produced, and, furthermore, can provide for sensitive detection of very small amounts of materials. The subject devices can be used to determine small compounds, large compounds, aggregations of compounds, such as may be found in cellular debris, microorganisms, cells, or the like. The multiplicity of measuring sites or pixels allows for great flexibility in employing a variety of different measurements in conjunction with standards, to ensure accurate quantitative results.

Although the foregoing invention has been described in some detail by way of illustration and example for purposes of clarity of understanding, it will be obvious that certain changes and modifications may be practiced within the scope of the appended claims.

What is claimed is:

1. An apparatus for making a plurality of determinations at different sites, of an electrically conductive substance capable of modifying the capacitance of a semiconductor, comprising:
   a semiconductor;
   an insulating layer, having a substantially constant predetermined capacitance and being substantially inert to said substance, said insulating layer overlaying one surface of said semiconductor at a plurality of sites;
   means for retaining said electrically conductive substance in communication with at least one of said plurality of sites;
   a counter electrode electrically coupled to said electrically conductive substance;
   means for measuring the capacitance across said semiconductor and said insulating layer at each of said sites;
   means for isolating the capacitance at each site from the capacitance at each of the other sites, wherein said means for isolating comprises a plurality of counter electrode plates, each of said plates being proximate one of said sites;
   means adapted for providing high electrical impedance between said plates; and
   switching means for sequentially coupling each of said plates to said capacitance measuring means.

2. The apparatus of claim 1, wherein said means adapted for providing high electrical impedance comprises at least one shallow and/or thin channel separating said plates such that said media is spread in small cross-section to reduce conductance from plate to plate.

3. The apparatus of claim 1, wherein said means adapted for providing high electrical impedance comprises container means for holding electrically conductive substance having some resistance in contact with said plates so as to provide a smaller resistance between each of the counter electrode plates and the insulative layer of the semiconductor electrode compared to the resistance between individual counter electrode plates.

4. An apparatus for making a plurality of determinations at different sites, of an electrically conductive substance capable of modifying the capacitance of a semiconductor, comprising:
   a semiconductor;
   an insulating layer, having a substantially constant predetermined capacitance and being substantially inert to said substance, said insulating layer overlaying one surface of said semiconductor at a plurality of sites;
   means for retaining said electrically conductive substance in communication with at least one of said plurality of sites;
   a counter electrode electrically coupled to said electrically conductive substance;
   means for measuring the capacitance across said semiconductor and said insulating layer at each of said sites;
   means for isolating the capacitance at each site from the capacitance at each of the other sites, wherein said means for isolating the capacitance at each site comprises a doped portion of said semiconductor proximate one of said sites, wherein an area around said doped portion is eroded to isolate said portion from other doped portions, said further comprising a plurality of insulating regions, each insulating region being between one of said doped portions and said semiconductor;
   means adapted for providing high electrical impedance between said plates; and
   switching means for sequentially coupling each of said plates to said capacitance measuring means.

5. An apparatus for making a plurality of determinations at different sites, of an electrically conductive substance capable of modifying the capacitance of a semiconductor, comprising:
   a semiconductor;
   an insulating layer, having a substantially constant predetermined capacitance and being substantially inert to said substance, said insulating layer overlaying one surface of said semiconductor at a plurality of sites;
   means for retaining said electrically conductive substance in communication with at least one of said plurality of sites;
   a counter electrode electrically coupled to said electrically conductive substance;
   means for measuring the capacitance across said semiconductor and said insulating layer at each of said sites;
   means for isolating the capacitance at each site from the capacitance at each of the other sites;
   means adapted for providing high electrical impedance between said plates;
   switching means for sequentially coupling each of said plates to said capacitance measuring means; and
   a reference electrode electrically coupled to said electrically conductive substance.

6. An apparatus for making a plurality of determinations at different sites, of an electrically conductive substance capable of modifying the capacitance of a semiconductor, comprising:
   a semiconductor;

an insulating layer, having a substantially constant predetermined capacitance and being substantially inert to said substance, said insulating layer overlaying one surface of said semiconductor at a plurality of sites;

means for retaining said electrically conductive substance in communication with at least one of said plurality of sites;

a counter electrode electrically coupled to said electrically conductive substance;

means for measuring the capacitance across said semiconductor and said insulating layer at each of said sites, wherein said capacitance measuring means comprises;

means for providing an alternating voltage across said semiconductor and said counter electrode; and means for measuring the alternating current responsive to said alternating voltage;

means for isolating the capacitance at each site from the capacitance at each of the other sites;

means adapted for providing high electrical impedance between said plates;

switching means for sequentially coupling each of said plates to said capacitance measuring means; and means for applying a DC bias potential across said semiconductor and counter electrode.

7. The apparatus of claim 6, further comprising means for varying said DC bias potential in order to maintain said alternating current constant.

8. The apparatus of claim 7, wherein said means for varying comprises:

means for filtering said alternating current to produce a filtered signal;

means for rectifying said filtered signal to produce a rectified signal;

means for amplifying said rectified signal to provide a feedback signal; and means, responsive to said feedback signal, for altering said DC bias potential.

9. An apparatus for making a plurality of determination at different sites, of an electrically conductive substance capable of modifying the capacitance of a semiconductor, comprising:

a monolithic semiconductor wafer;

a plurality of doped regions in said semiconductor wafer, each of said regions being proximate one of said sites;

an insulating layer, having a substantially constant predetermined capacitance and being substantially inert to said substance, said insulating layer overlaying said doped regions;

means for retaining said electrically conductive substance in communication with at least one of said sites;

a counter electrode positioned to contact said electrically conductive substance;

means for measuring the capacitance across said doped regions and said insulating layer, wherein said means for measuring comprises;

means for providing an alternating voltage across said semiconductor and said counter electrode; and means for measuring the alternating current responsive to said alternating voltage;

means for applying a DC bias potential across said doped regions and said counter electrode;

means for filtering said alternating current;

means for reifying said alternating current;

means for amplifying said filtered, rectified alternating current to provide a feedback signal; and means, responsive to said feedback signal, for varying said DC bias potential to maintain said alternating current constant.

10. The apparatus of claim 9, further comprising reference electrode means electrically coupled to said electrically conductive substance for measuring the DC bias potential applied across said electrically conductive substance and said doped regions.

* * * * *